United States Patent
Chen et al.

(10) Patent No.: US 9,632,038 B2
(45) Date of Patent: Apr. 25, 2017

(54) HYBRID PHASE UNWRAPPING SYSTEMS AND METHODS FOR PATTERNED WAFER MEASUREMENT

(71) Applicant: KLA-Tencor Corporation, Milpitas, CA (US)

(72) Inventors: Haiguang Chen, Mountain View, CA (US); Jaydeep Sinha, Livermore, CA (US)

(73) Assignee: KLA-Tencor Corporation, Milpitas, CA (US)

(*) Notice: Subject to any disclaimer, the term of this patent is extended or adjusted under 35 U.S.C. 154(b) by 70 days.

(21) Appl. No.: 14/808,994

(22) Filed: Jul. 24, 2015

(65) Prior Publication Data
US 2016/0321799 A1    Nov. 3, 2016

Related U.S. Application Data

(60) Provisional application No. 62/039,769, filed on Aug. 20, 2014.

(51) Int. Cl.
*G01N 21/95* (2006.01)
*G01B 11/24* (2006.01)
(Continued)

(52) U.S. Cl.
CPC ......... *G01N 21/9501* (2013.01); *G01B 11/06* (2013.01); *G01B 11/2441* (2013.01);
(Continued)

(58) Field of Classification Search
CPC  G01N 21/9501; G01B 11/06; G01B 11/2441; G06T 2207/30148
See application file for complete search history.

(56) References Cited

U.S. PATENT DOCUMENTS 6,028,670 A * 2/2000 Deck ............... G01B 11/2441
356/497
6,738,511 B1 * 5/2004 Farrell ............ G01B 9/02083
382/168
(Continued)

FOREIGN PATENT DOCUMENTS

WO    2011085019 A2    7/2011

OTHER PUBLICATIONS

R. Gappinger, J. Greivenkamp, and C. Borman, "High-modulation camera for use with a non-null interferometer", Opt. Eng. 43 (3) 689-696, Mar. 2004.
(Continued)

*Primary Examiner* — Wesley Tucker
(74) *Attorney, Agent, or Firm* — Sulter Swantz pc llo

(57) ABSTRACT

Systems and methods for unwrapping phase signals obtained from interferometry measurements of patterned wafer surfaces are disclosed. A phase unwrapping method in accordance with the present disclosure may calculate a front surface phase map and a back surface phase map of a wafer, subtract the back surface phase map from the front surface phase map to obtain a phase difference map, unwrap the phase difference map to obtain a wafer thickness variation map, unwrap the back surface phase map to obtain a back surface map representing the back surface of the wafer; and add the wafer thickness variation map to the back surface phase map to calculate a front surface map representing the front surface of the wafer.

21 Claims, 7 Drawing Sheets

FRONT PHASE

BACK PHASE

DIFFERENCE PHASE

(51) Int. Cl.
*G01B 11/06* (2006.01)
*G01N 21/88* (2006.01)
*G06T 7/00* (2017.01)

(52) U.S. Cl.
CPC ....... *G01N 21/8851* (2013.01); *G06T 7/0004* (2013.01); *G01N 2201/06113* (2013.01); *G01N 2201/12* (2013.01); *G06T 2207/10056* (2013.01); *G06T 2207/30148* (2013.01)

(56) References Cited

U.S. PATENT DOCUMENTS

| | | | |
|---|---|---|---|
| 6,847,458 B2 | 1/2005 | Freischlad et al. | |
| 7,667,852 B2 | 2/2010 | Tang | |
| 7,847,954 B2 | 12/2010 | Tang et al. | |
| 8,126,677 B2 | 2/2012 | De Groot et al. | |
| 8,643,847 B1 * | 2/2014 | Chen | G01B 9/0203 356/511 |
| 9,074,873 B1 * | 7/2015 | Tang | G01B 11/06 |
| 9,121,684 B2 * | 9/2015 | Tang | G01B 9/02076 |
| 2002/0135775 A1 * | 9/2002 | De Groot | G01B 11/0608 356/497 |
| 2007/0115484 A1 * | 5/2007 | Huang | G01B 11/2504 356/604 |

OTHER PUBLICATIONS

J. Greivenkamp and A. Lowman, "Modulation transfer function measurement of sparse-array sensors using a self-calibrating fringe pattern," Appl. Opt. 33(22). 5029-5036, Aug. 1994.
PCT International Search Report for International Application No. PCT/US2016/042592 dated Nov. 1, 2016, 3 Pages.

* cited by examiner

HYBRID PHASE UNWRAPPING SYSTEMS AND METHODS FOR PATTERNED WAFER MEASUREMENT

TECHNICAL FIELD

The disclosure generally relates to the field of wafers, and particularly to systems and methods for effective phase unwrapping and accurate reconstruction of patterned wafer surface topography.

BACKGROUND

Thin polished plates such as silicon wafers and the like are a very important part of modern technology. A wafer, for instance, may refer to a thin slice of semiconductor material used in the fabrication of integrated circuits and other devices. Other examples of thin polished plates may include magnetic disc substrates, gauge blocks and the like. While the technique described here refers mainly to wafers, it is to be understood that the technique also is applicable to other types of polished plates as well. The term wafer and the term thin polished plate may be used interchangeably in the present disclosure.

Wafers are available in a variety of sizes. They may also be patterned or presented as bare wafers. Interferometer wafer metrology systems, such as WaferSight metrology system from KLA-Tencor, may scan both the front and back surfaces of a wafer at the same time. By combining wafer shape, edge roll-off, thickness or flatness, and topography measurements in a single scan, such wafer metrology tools may provide complete data sets that are necessary for topography and wafer geometry monitoring in wafer manufacturing.

It is noted, however, that most existing interferometer wafer metrology systems reconstruct the wafer surface by calculating the wrapped surface phase maps from a sequence of measured interferometry image frames and then unwrapping these phase maps for the wafer surface height maps. It is noted that the general two dimensional phase unwrapping for wafer surface height maps may introduce errors and failures have been observed when attempting to reconstruct wafer surface maps of patterned wafers. More specifically, phase signals of a patterned wafer surface obtained using a wafer metrology tool typically contain sharp phase transitions induced by the wafer surface pattern structures. These sharp phase transitions often lead to phase unwrapping errors, which in turn may cause severe artifacts on a reconstructed wafer surface map.

Phase unwrapping methods based on global gradient matching optimization, such as minimum norm phase unwrapping or the like, may be able to provide more robust and accurate phase unwrapping results for patterned wafers. However, such phase unwrapping methods require gradient matching of the acquired wafer surface phase and the reconstructed wafer surface, and also require the phase aliasing errors to be kept small. When used directly on the phase maps obtained from measurements of large shape wafers, gradient matching optimization based phase unwrapping methods will generate large shape artifacts. Severe surface errors have been observed in the wafer areas with large shape slopes.

SUMMARY

The present disclosure is directed to a phase unwrapping method. The method may include: acquiring at least one image of a front surface of a wafer and at least one image of a back surface of the wafer; calculating a front surface phase map for the wafer based on the at least one image of the front surface of the wafer; calculating a back surface phase map for the wafer based on the at least one image of the back surface of the wafer; subtracting the back surface phase map from the front surface phase map to obtain a phase difference map; phase unwrapping the phase difference map to obtain a wafer thickness variation map; phase unwrapping the back surface phase map to obtain a back surface map representing the back surface of the wafer; and adding the wafer thickness variation map to the back surface phase map to calculate a front surface map representing the front surface of the wafer.

A further embodiment of the present disclosure is directed to a system. The system may include at least one imaging device configured to acquire at least one image of a front surface of a wafer and at least one image of a back surface of the wafer. The system may also include at least one processor in communication with the at least one imaging device. The at least one processor may be configured to: calculate a front surface phase map for the wafer based on the at least one image of the front surface of the wafer; calculate a back surface phase map for the wafer based on the at least one image of the back surface of the wafer; subtract the back surface phase map from the front surface phase map to obtain a phase difference map; phase unwrap the phase difference map to obtain a wafer thickness variation map; phase unwrap the back surface phase map to obtain a back surface map representing the back surface of the wafer; and add the wafer thickness variation map to the back surface phase map to calculate a front surface map representing the front surface of the wafer.

An additional embodiment of the present disclosure is directed to a method. The method may include: acquiring at least one image of a front surface of a patterned wafer and at least one image of a back surface of the patterned wafer; calculating a front surface phase map for the wafer based on the at least one image of the front surface of the wafer; calculating a back surface phase map for the wafer based on the at least one image of the back surface of the wafer; subtracting the back surface phase map from the front surface phase map to obtain a phase difference map; phase unwrapping the phase difference map to obtain a wafer thickness variation map; phase unwrapping the back surface phase map to obtain a back surface map representing the back surface of the wafer; performing phase congruency on the wafer thickness variation map; and adding the wafer thickness variation map to the back surface phase map to calculate a front surface map representing the front surface of the wafer.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

The present disclosure is directed to systems and methods that can be utilized to effectively unwrap phase signals from interferometry measurements of patterned wafer surfaces and to accurately reconstruct the wafer surface topography. More specifically, in accordance with the present disclosure, a phase difference map may be calculated based on front and back phase differences, which may then be utilized to improve accuracy of phase unwrapping.

Figure 1:
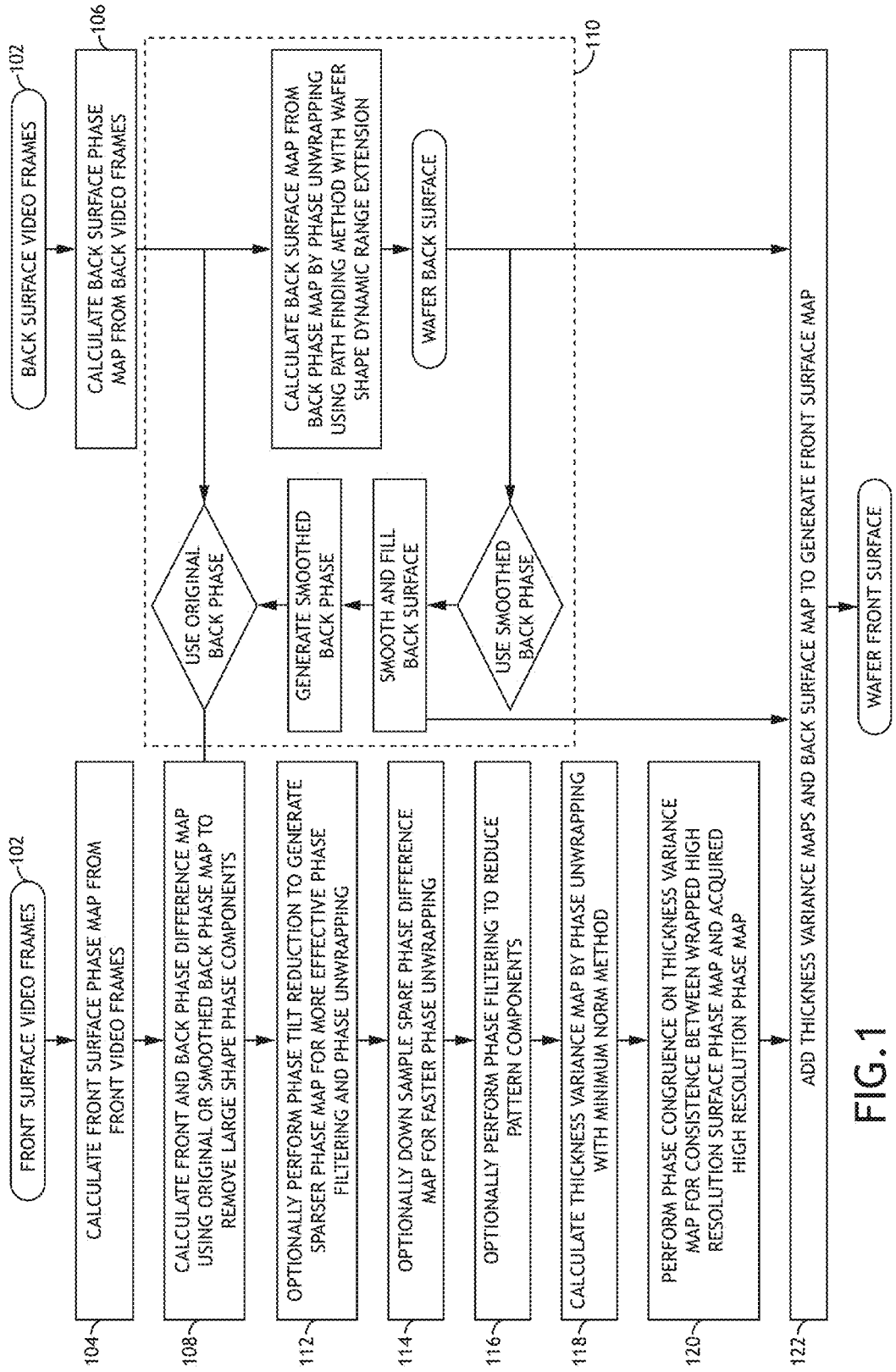
FIG. 1 is a flow diagram illustrating a hybrid phase unwrapping method.

Referring generally to FIG. 1, a flow diagram illustrating a hybrid phase unwrapping method 100 in accordance with an embodiment of the present disclosure is shown. More specifically, a wafer metrology tool may be utilized to acquire both the front and back surface image/video frames of the wafer in step 102. Steps 104 and 106 may then be carried out to calculate the front and back phase maps of the wafer based on the acquired video frames, respectively.

Figure 2:
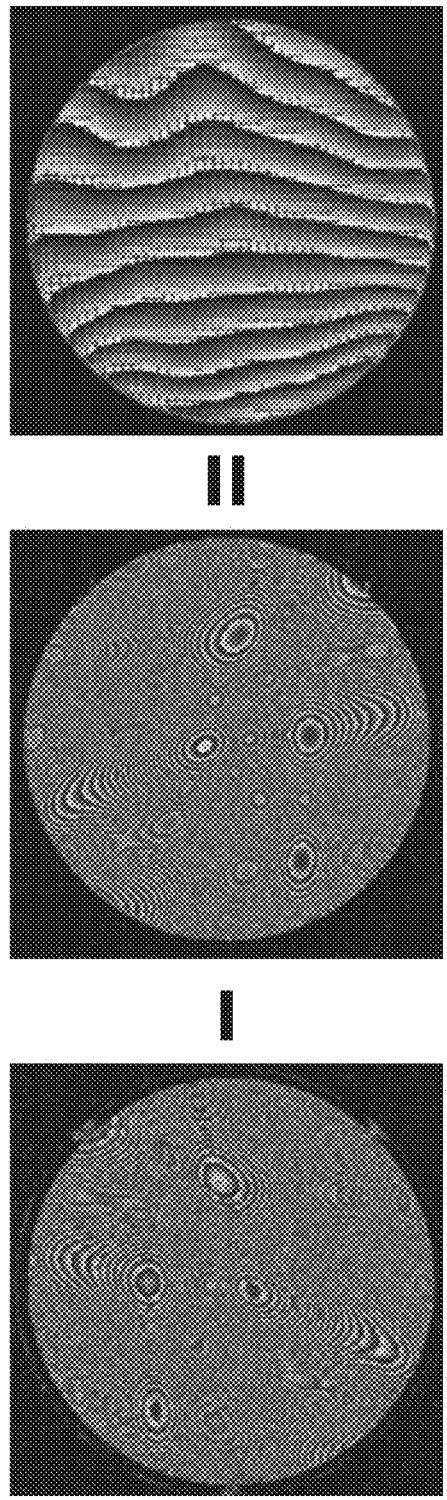
FIG. 2 is an illustration depicting calculation of an exemplary phase difference map.

Once the front and back phase maps of the wafer have been calculated, step 108 may calculate a phase difference map by subtracting the back phase map, after left-right flipping the back surface phase map and center aligning it with the front phase map, from the front phase map to remove large shape phase components. FIG. 2 is a depiction of an exemplary phase difference map. It is noted that the resulting phase difference map may represent the phase components of the wafer thickness variation in the range of a few microns, and the phase difference map may have much sparse phase fringes and much lower phase slopes, effectively removing the phase aliasing errors in the original front and back phase maps generated from the wafer surfaces with large shape slopes.

It is also noted that the back phase map utilized to calculate the phase difference map may be the original back phase map (calculated in step 106) or a smoothed back phase map (depicted as a part of step 110) if smoothing the back phase map is deemed necessary. For instance, if it is determined that the back surface contains sharp and/or high magnitude height variations (e.g., laser marks or other large surface defects) that cause large variations in the back surface phase map, these large sharp back phase components may be deemed in violation of the requirement of having a smooth back surface to serve as a reference for the front surface phase unwrapping. In these cases, step 110 may be carried out to further smooth the back phase map. It is to be understood that the detailed implementation of the smoothing technique depicted in FIG. 1 is exemplary; it is contemplated that other techniques may be utilized to smooth the back phase map without departing from the spirit and scope of the present disclosure.

Figure 3:
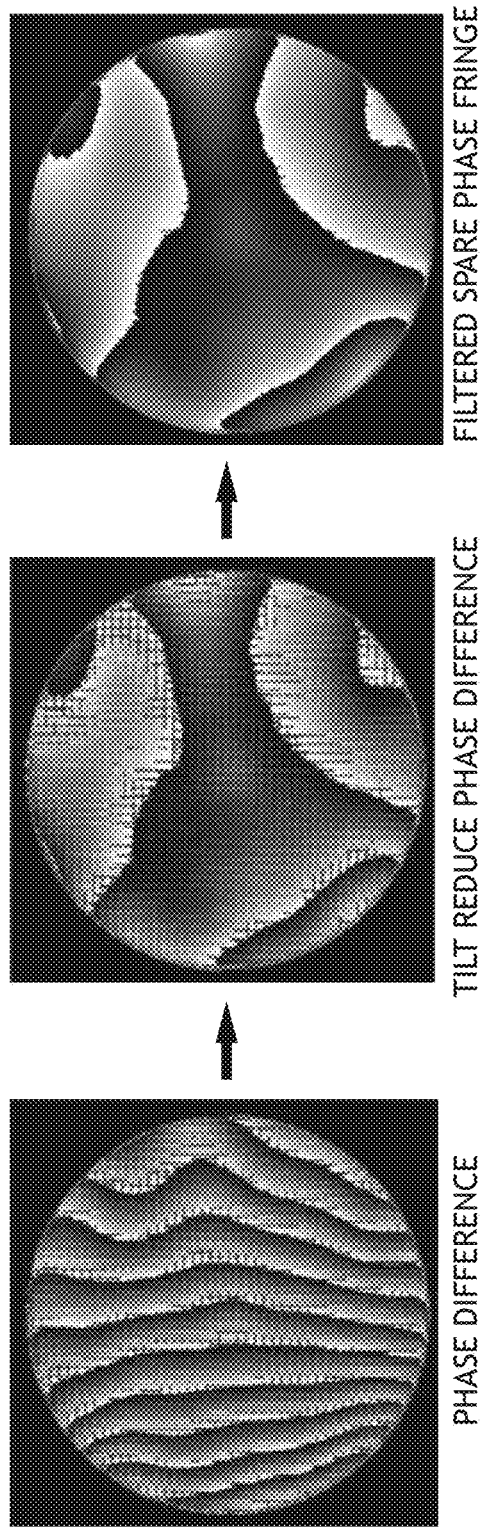
FIG. 3 is an illustration depicting application of phase tilt reduction and low-pass filtering to a phase difference map.

It is also contemplated that one or more optional steps 112-116 may be carried out to further condition the calculated phase difference map. For instance, as shown in FIGS. 1 and 3, an optional step 112 may be utilized to perform phase tilt reduction on the phase difference map to further reduce the phase fringe spacing and thus the phase slop. An optional step 114 may be utilized to down sample the phase difference map in order to obtain a smaller image size for a faster processing time. In addition, an optional step 116 may be utilized to apply proper filtering (e.g., low-pass filtering) to further suppress the pattern phase components for a more robust surface shape reconstruction.

It is noted that since steps 112-116 are presented as optional steps, whether to carry out one or more of such steps may depend on specific operating conditions and availability of various resources, and it is contemplated that specific implementations of steps 112-116 may vary.

Once the phase difference map is calculated (step 108) and optionally conditioned (steps 112-116), step 118 may phase unwrap the phase difference map to obtain a wafer thickness variation map. If the phase unwrapping step 118 is performed on a down sampled phase difference map (i.e., step 114 was invoked), an interpolation step may be performed to map the reconstructed thickness variation map to the original high resolution thickness variation map. It is contemplated that the minimum norm phase unwrapping technique may be utilized to phase unwrap the phase difference map. It is also contemplated, however, that other phase unwrapping techniques may be utilized without departing from the spirit and scope of the present disclosure.

Subsequently, step 120 may perform phase congruency on the wafer thickness variation map so that the final reconstructed surface may have consistent phase values with the original high resolution phase difference map. The resulting wafer thickness variation map may then be utilized to reconstruct the wafer surface in step 122.

Figure 4:
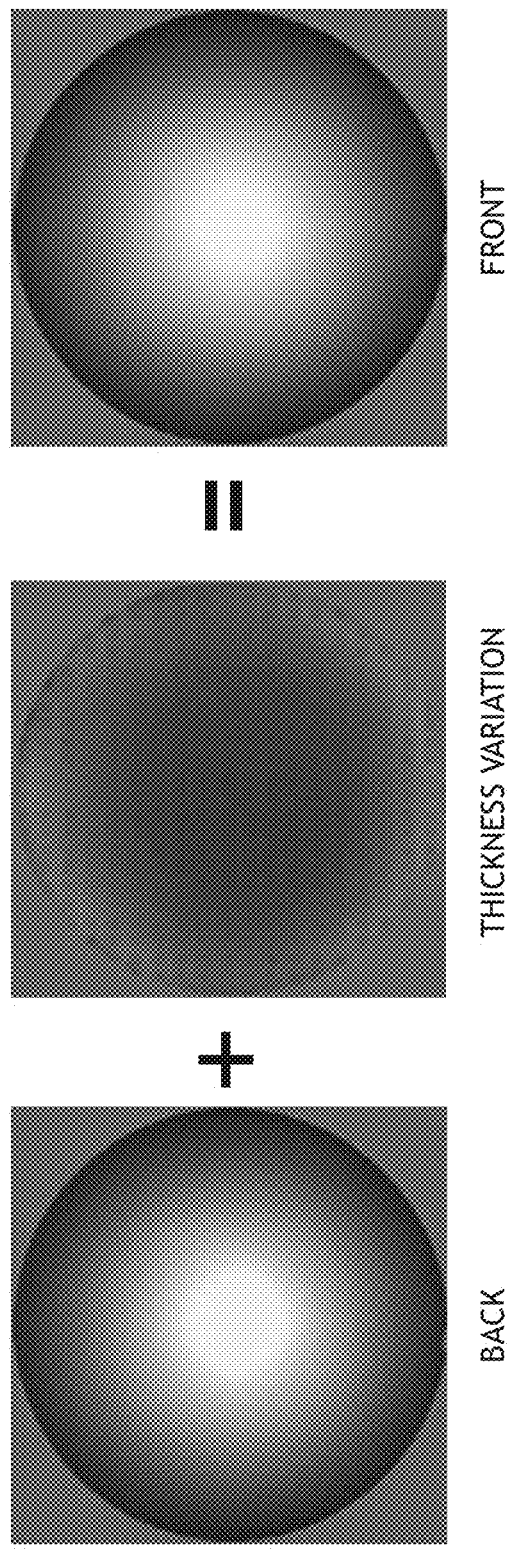
FIG. 4 is an illustration depicting reconstruction of a wafer surface map.

In certain implementations, the wafer back surface may be reconstructed first using the back surface phase map calculated in step 106. The wafer back surface may be reconstructed using existing techniques such as path finding with wafer shape dynamic range extension or the like. If the back phase map was smoothed (as previously mentioned), the wafer back surface may be reconstructed using the path following phase unwrapping algorithm with the slope dynamic range extension to extend the surface slope beyond the Nyquist slope sampling rate so that the large shape smooth back surface can be obtained. In either case, once the wafer back surface is reconstructed, the wafer thickness variation map may be added to the reconstructed wafer back surface to generate the patterned wafer front surface, as shown in FIG. 4.

Figure 5:
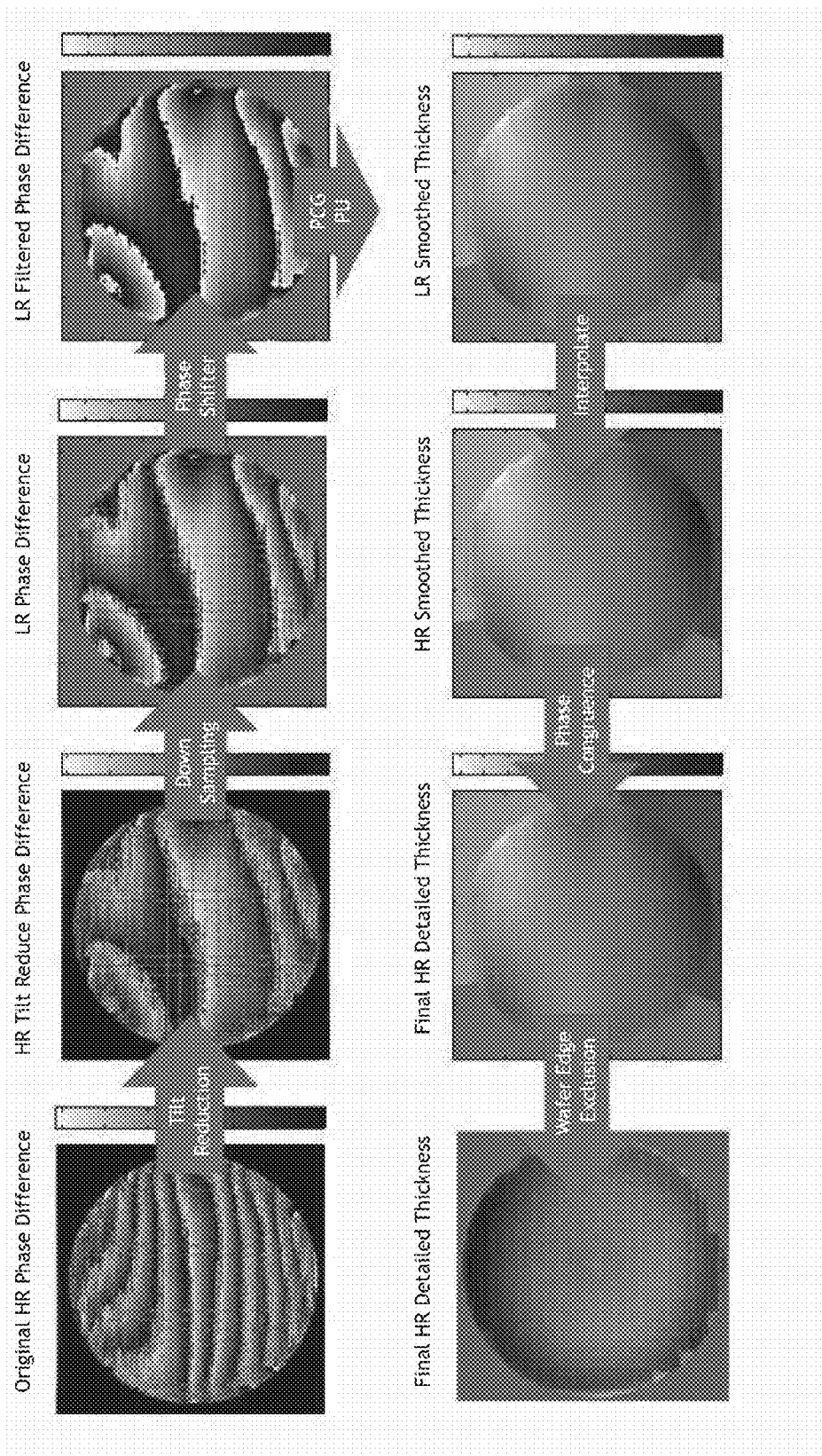
FIG. 5 is an illustration depicting an exemplary process flow of a phase difference map, including tilt reduction, down sampling, interpolation, and phase congruency.

Experimental results indicate that the phase unwrapping method 100 described above can be performed accurately in a timely manner. It is also noted that processing speed (or throughput) may be further improved using the down sampling techniques previous mentioned (step 114). For instance, many patterned wafers may have slow wafer thickness variations across the wafer surface and their local pattern components may have small phase magnitudes. In these cases, down sampled low resolution (LR) phase difference maps may be used for the generation of the initial wafer thickness variation map and high resolution (HR) pattern components may be restored in the final high resolution phase congruency stage as shown in the processing sequence depicted in FIG. 5 (which corresponds to the flow diagram shown in FIG. 1). Test results indicate that using down sampling techniques in the manner described above produce very accurate results with significant process time reductions, which may be appreciated especially in high volume chip manufacturing processes.

Figure 6:
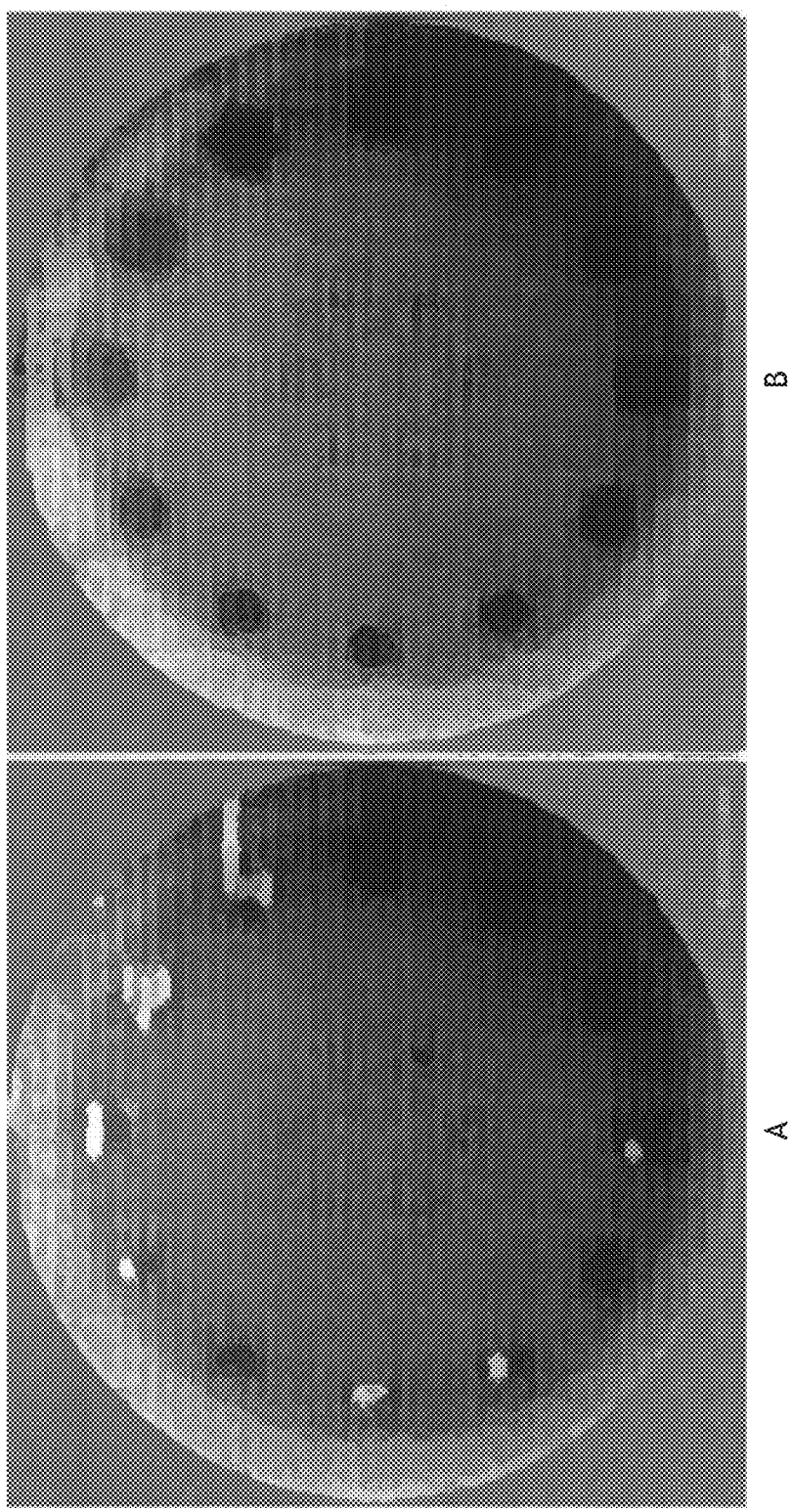
FIG. 6 is an illustration depicting differences between a wafer thickness map produced without down sampling and a wafer thickness map produced with down sampling.

It is contemplated that down sampling may also provide other advantages in addition to improved system throughput. For instance, certain wafer surfaces may have very large shape variations, which may be better handled utilizing a two-resolution process. Referring to FIG. 6, the wafer thickness map A is produced without down sampling while the wafer thickness map B is produced with down sampling. It is noted that the phase unwrapping errors in map A have been greatly reduced in map B due to the extra phase signal filtering induced in the phase map down sampling process, and the resulting features on the reconstructed wafer surface can be more accurately identified in map B.

It is to be understood that the phase unwrapping method 100 described herein may provide other advantages that have not been explicitly identified in the present disclosure. For instance, the phase difference map helps remove phase components from large wafer shape components and therefore effectively remove the phase aliasing errors. The phase difference map can also be used in the phase unwrapping methods based on other global optimization to generate the wafer thickness variation map, which has very low shape dynamic range limited by the wafer thickness variations. The path following phase unwrapping may be used to unwrap the phase signal from smooth wafer back surface and perform dynamic range extension on smooth phase slope maps. When necessary, the smoothed wafer back surface and/or an estimated initial front wafer surface (e.g., estimated using other alternative methods) can be used to generate a reference phase map and used to remove phase aliasing errors from large wafer shape variations.

Figure 7:
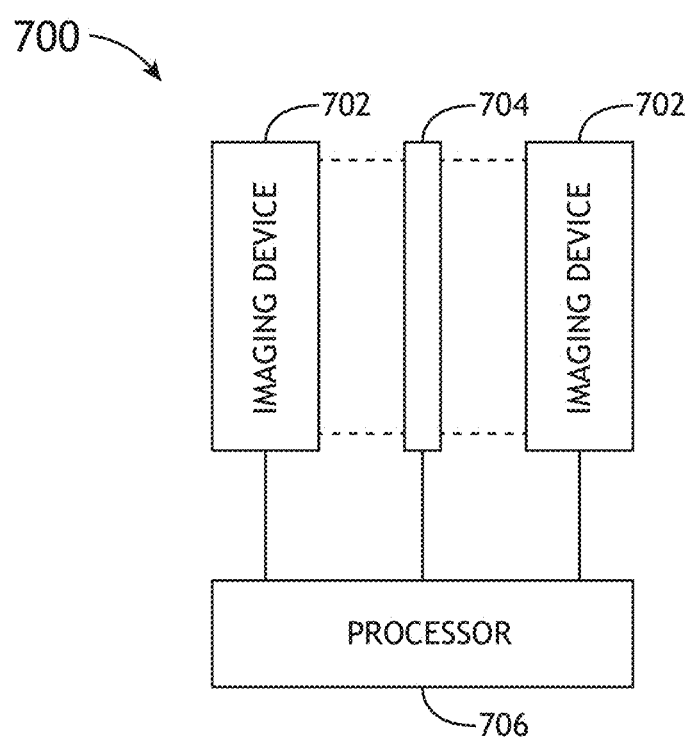
FIG. 7 is a block diagram depicting a wafer metrology tool.

Referring now to FIG. 7, a block diagram depicting a wafer metrology tool 700 capable of performing the phase unwrapping method 100 described above is shown. The wafer metrology tool 700 may include one or more imaging devices (e.g., cameras, scanners, microscopes, interferometers or the like) 702 configured to acquire front and back surface image/video frames of a wafer 704.

Data acquired by the imaging device 702 may then be provided to a processor 706 configured to processing the acquired data. The processor 706 may be implemented utilizing any standalone or embedded computing device (e.g., a computer, a processing unit/circuitry or the like). Upon receiving the data from the imaging device 702, the processor 706 may process the received data to unwrap phase signals and reconstruct the wafer surface topography as described above.

It is contemplated that the wafer metrology tool 700 may be implemented as a part of an interferometer system, such as WaferSight metrology system from KLA-Tencor. It is also contemplated that the interferometer system may implement measurement techniques such as those described in: Method and Apparatus for Measuring the Shape and Thickness Variation of a Wafer with a Large Warp, U.S. Provisional Patent Application Ser. No. 62/039,769, filed Aug. 20, 2014, which is herein incorporated by reference in its entirety. It is noted that such an interferometer system may utilize two or more wavelength tunable lasers (or one tunable laser capable of tuning in two or more wavelength bands) to provide two- or multi-wavelength phase shift interferometry that can provide extended dynamic ranges without losing measurement accuracy. It is contemplated that such interferometer systems may be appreciated for their abilities to provide fast and accurate measurements for patterned wafers and/or wafers with large warps.

It is understood that while the examples above referred to patterned wafers as being particularly challenging for existing wafer measurement tools to handle, the systems and methods in accordance with the present disclosure are not limited to processing patterned wafers. The systems and methods in accordance with the present disclosure are applicable to other types of polished plates as well without departing from the spirit and scope of the present disclosure. The term wafer used in the present disclosure may include a thin slice of semiconductor material used in the fabrication of integrated circuits and other devices, as well as other thin polished plates such as magnetic disc substrates, gauge blocks and the like.

The methods disclosed may be implemented as sets of instructions, through a single processing device, and/or through multiple processing devices. Further, it is understood that the specific order or hierarchy of steps in the methods disclosed are examples of exemplary approaches. Based upon design preferences, it is understood that the specific order or hierarchy of steps in the method can be rearranged while remaining within the scope and spirit of the disclosure. The accompanying method claims present elements of the various steps in a sample order, and are not necessarily meant to be limited to the specific order or hierarchy presented.

It is believed that the system and method of the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory.

What is claimed is:

1. A method, comprising:
   acquiring at least one image of a front surface of a wafer and at least one image of a back surface of the wafer;
   calculating a front surface phase map for the wafer based on the at least one image of the front surface of the wafer;
   calculating a back surface phase map for the wafer based on the at least one image of the back surface of the wafer;
   subtracting the back surface phase map from the front surface phase map to obtain a phase difference map;
   phase unwrapping the phase difference map to obtain a wafer thickness variation map;
   phase unwrapping the back surface phase map to obtain a back surface map representing the back surface of the wafer; and
   adding the wafer thickness variation map to the back surface phase map to calculate a front surface map representing the front surface of the wafer.

2. The method of claim 1, wherein the front surface of the wafer is patterned.

3. The method of claim 1, further comprising:
   smoothing the back surface phase map prior to subtracting the back surface phase map from the front surface phase map to obtain the phase difference map.

4. The method of claim 1, further comprising:
   performing phase tilt reduction on the phase difference map prior to phase unwrapping the phase difference map to obtain the wafer thickness variation map.

5. The method of claim 1, further comprising:
performing phase filtering on the phase difference map prior to phase unwrapping the phase difference map to obtain the wafer thickness variation map.

6. The method of claim 1, further comprising:
down sampling the phase difference map from a higher resolution to a lower resolution prior to phase unwrapping the phase difference map to obtain the wafer thickness variation map.

7. The method of claim 6, further comprising:
interpolating the wafer thickness variation map from the lower resolution to the higher resolution prior to adding the wafer thickness variation map to the back surface phase map to calculate the front surface map representing the front surface of the wafer.

8. The method of claim 1, further comprising:
performing phase congruency on the wafer thickness variation map prior to adding the wafer thickness variation map to the back surface phase map to calculate the front surface map representing the front surface of the wafer.

9. A system, comprising:
at least one imaging device configured to acquire at least one image of a front surface of a wafer and at least one image of a back surface of the wafer;
at least one processor in communication with the at least one imaging device, the at least one processor configured to:
calculate a front surface phase map for the wafer based on the at least one image of the front surface of the wafer;
calculate a back surface phase map for the wafer based on the at least one image of the back surface of the wafer;
subtract the back surface phase map from the front surface phase map to obtain a phase difference map;
phase unwrap the phase difference map to obtain a wafer thickness variation map;
phase unwrap the back surface phase map to obtain a back surface map representing the back surface of the wafer; and
add the wafer thickness variation map to the back surface phase map to calculate a front surface map representing the front surface of the wafer.

10. The system of claim 9, wherein the at least one processor is further configured to:
smooth the back surface phase map prior to subtract the back surface phase map from the front surface phase map to obtain the phase difference map.

11. The system of claim 9, wherein the at least one processor is further configured to:
perform phase tilt reduction on the phase difference map prior to phase unwrap the phase difference map to obtain the wafer thickness variation map.

12. The system of claim 9, wherein the at least one processor is further configured to:
perform phase filtering on the phase difference map prior to phase unwrap the phase difference map to obtain the wafer thickness variation map.

13. The system of claim 9, wherein the at least one processor is further configured to:
down sample the phase difference map from a higher resolution to a lower resolution prior to phase unwrap the phase difference map to obtain the wafer thickness variation map.

14. The system of claim 13, wherein the at least one processor is further configured to:
interpolate the wafer thickness variation map from the lower resolution to the higher resolution prior to add the wafer thickness variation map to the back surface phase map to calculate the front surface map representing the front surface of the wafer.

15. The system of claim 9, wherein the at least one processor is further configured to:
perform phase congruency on the wafer thickness variation map prior to add the wafer thickness variation map to the back surface phase map to calculate the front surface map representing the front surface of the wafer.

16. A method, comprising:
acquiring at least one image of a front surface of a patterned wafer and at least one image of a back surface of the patterned wafer;
calculating a front surface phase map for the wafer based on the at least one image of the front surface of the wafer;
calculating a back surface phase map for the wafer based on the at least one image of the back surface of the wafer;
subtracting the back surface phase map from the front surface phase map to obtain a phase difference map;
phase unwrapping the phase difference map to obtain a wafer thickness variation map;
phase unwrapping the back surface phase map to obtain a back surface map representing the back surface of the wafer;
performing phase congruency on the wafer thickness variation map; and
adding the wafer thickness variation map to the back surface phase map to calculate a front surface map representing the front surface of the wafer.

17. The method of claim 16, further comprising:
smoothing the back surface phase map prior to subtracting the back surface phase map from the front surface phase map to obtain the phase difference map.

18. The method of claim 16, further comprising:
performing phase tilt reduction on the phase difference map prior to phase unwrapping the phase difference map to obtain the wafer thickness variation map.

19. The method of claim 16, further comprising:
performing phase filtering on the phase difference map prior to phase unwrapping the phase difference map to obtain the wafer thickness variation map.

20. The method of claim 16, further comprising:
down sampling the phase difference map from a higher resolution to a lower resolution prior to phase unwrapping the phase difference map to obtain the wafer thickness variation map.

21. The method of claim 20, further comprising:
interpolating the wafer thickness variation map from the lower resolution to the higher resolution prior to adding the wafer thickness variation map to the back surface phase map to calculate the front surface map representing the front surface of the wafer.

* * * * *